US012226473B2

(12) United States Patent
Zhou et al.

(10) Patent No.: US 12,226,473 B2
(45) Date of Patent: Feb. 18, 2025

(54) SARS-COV-2 ANTIGEN POLYPEPTIDE, RECOMBINANT ADENO-ASSOCIATED VIRUS EXPRESSING THE POLYPEPTIDE, AND VACCINE CONTAINING THE VIRUS

(71) Applicant: Hengda Biomedical Technology Co., Ltd., Guangdong (CN)

(72) Inventors: Zexin Zhou, Guangdong (CN); Zhongqiu Liu, Guangdong (CN); Guochao Liao, Guangdong (CN); Huapeng Li, Guangdong (CN); Chao Zhang, Guangdong (CN); Xiaoxiao Qi, Guangdong (CN); Junlin Chen, Guangdong (CN); Deying Yang, Guangdong (CN)

(73) Assignee: Hengda Biomedical Technology Co., Ltd., Guangzhou (CN)

( * ) Notice: Subject to any disclaimer, the term of this patent is extended or adjusted under 35 U.S.C. 154(b) by 793 days.

(21) Appl. No.: 17/327,784

(22) Filed: May 24, 2021

(65) Prior Publication Data

US 2021/0346493 A1 Nov. 11, 2021

Related U.S. Application Data

(63) Continuation-in-part of application No. PCT/CN2020/127311, filed on Nov. 7, 2020.

(30) Foreign Application Priority Data

May 11, 2020 (CN) ........................ 202010392553.1

(51) Int. Cl.

| | |
|---|---|
| ***C12N 15/86*** | (2006.01) |
| ***A61K 39/12*** | (2006.01) |
| ***A61K 39/215*** | (2006.01) |
| ***C07K 14/165*** | (2006.01) |
| ***C12N 7/00*** | (2006.01) |

(52) U.S. Cl.

CPC .......... *A61K 39/215* (2013.01); *C07K 14/165* (2013.01); *C12N 7/00* (2013.01); *C12N 15/86* (2013.01); *C07K 2319/02* (2013.01); *C12N 2750/14134* (2013.01); *C12N 2750/14143* (2013.01); *C12N 2750/14151* (2013.01)

(58) Field of Classification Search

None

See application file for complete search history.

(56) References Cited

U.S. PATENT DOCUMENTS

2018/0243416 A1* 8/2018 Limberis .............. A61K 39/145

FOREIGN PATENT DOCUMENTS

CN 107245475 A 10/2017
CN 108699567 A 10/2018

OTHER PUBLICATIONS

NCBI Reference Sequence: YP_009824390.1 (Mar. 30, 2020). (Year: 2020).*
GenBank accession: NC_045512.2 (Mar. 30, 2020). (Year: 2020).*
Du, et al. J Immunol. Jan. 15, 2008;180(2):948-56. doi: 10.4049/jimmunol.180.2.948. PMID: 18178835. (Year: 2008).*
GenBank Accession WKP41103 (Oct. 30, 2023) (Year: 2023).*
GenBank Accession OR311786.1 (Oct. 30, 2023) (Year: 2023).*
Alexandra C. Walls et al., Structure, Function, and Antigenicity of the SARS-CoV-2 Spike Glycoprotein, Cell, Apr. 16, 2020, pp. 281-292, vol. 180.
Chain E, Spike protein S1, PDB: 6M17_E, Protein sequence data retrieved from GenPept, Mar. 12, 2021.
Renhong Yan et al., Structural basis for the recognition of the SARS-CoV-2 by full-length human ACE2, Science, Mar. 27, 2020, pp. 1444-1448, vol. 367, No. 6485.
Severe acute respiratory syndrome coronavirus 2 isolate Wuhan-Hu-1, complete genome, NCBI Reference Sequence: NC_045512.2, Sequence data retrieved from Genbank, Jul. 18, 2020.
Shelley A. Nass et al., Universal Method for the Purification of Recombinant AAV Vectors of Differing Serotypes, Molecular Therapy: Methods & Clinical Development, Jun. 2018, pp. 33-46, vol. 9.

* cited by examiner

*Primary Examiner* — Agnieszka Boesen

(57) ABSTRACT

Disclosed are a SARS-COV-2 antigen polypeptide, a recombinant adeno-associated virus (rAAV) expressing the polypeptide, and a vaccine containing the virus. A sequence of the antigen polypeptide is shown in SEQ ID NO: 1 and SEQ ID NO: 2. A method for preparing the recombinant adeno-associated virus comprises co-incubating pHelper, pRep2Cap5, and an expression vector, transfecting a cell in the presence of polyethyleneimine as a transfection reagent; culturing the cell, then collecting the cell by centrifugation, performing lysis and purification to obtain a purified liquid comprising the recombinant adeno-associated virus. The rAAV is delivered and expressed in vivo to produce a fusion antigen polypeptide, induces the production of serum neutralizing antibodies, which have a neutralizing titer to the novel SARS-COV-2 coronavirus and are expressed continuously; the rAAV composition can be used to immunize humans against the novel coronavirus pneumonia COVID-19.

8 Claims, 5 Drawing Sheets

Specification includes a Sequence Listing.

SEQUENCE LISTING

```
<160> NUMBER OF SEQ ID NOS: 6

<210> SEQ ID NO 1
<211> LENGTH: 263
<212> TYPE: PRT
<213> ORGANISM: SARS-COV-2(Coronavirus)

<400> SEQUENCE: 1

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
        195                 200                 205

Val Asn Phe Asn Phe Asn Gly Leu Thr Gly Thr Gly Val Leu Thr Glu
    210                 215                 220

Ser Asn Lys Lys Phe Leu Pro Phe Gln Gln Phe Gly Arg Asp Ile Ala
225                 230                 235                 240

Asp Thr Thr Asp Ala Val Arg Asp Pro Gln Thr Leu Glu Ile Leu Asp
                245                 250                 255

Ile Thr Pro Cys Ser Phe Gly
            260


<210> SEQ ID NO 2
```

```
<211> LENGTH: 223
<212> TYPE: PRT
<213> ORGANISM: SARS-COV-2(Coronavirus)

<400> SEQUENCE: 2

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Ile Leu Asp Ile Thr Pro Cys Ser Phe Gly
1               5                   10


<210> SEQ ID NO 4
<211> LENGTH: 5023
<212> TYPE: DNA
<213> ORGANISM: Artificial Sequence
<220> FEATURE:
<223> OTHER INFORMATION: Synthetic

<400> SEQUENCE: 4

cctgcaggca gctgcgcgct cgctcgctca ctgaggccgc ccgggcgtcg ggcgaccttt      60

ggtcgcccgg cctcagtgag cgagcgagcg cgcagagagg gagtggccaa ctccatcact     120

aggggttcct gcggccattc ggtacaattc acgcgtcgac attgattatt gactagctct     180

ggtcgttaca taacttacgg taaatggccc gcctggctga ccgcccaacg acccccgccc     240
```

-continued

```
attgacgtca ataatgacgt atgttcccat agtaacgcca atagggactt tccattgacg    300
tcaatgggtg gagtatttac ggtaaactgc ccacttggca gtacatcaag tgtatcatat    360
gccaagtacg ccccctattg acgtcaatga cggtaaatgg cccgcctggc attatgccca    420
gtacatgacc ttatgggact ttcctacttg gcagtacatc tactcgaggc cacgttctgc    480
ttcactctcc ccatctcccc cccctcccca cccccaattt tgtatttatt tattttttaa    540
ttattttgtg cagcgatggg ggcggggggg gggggggggg gggcgcgcgc caggcggggc    600
ggggcggggc gaggggcggg gcggggcgag gcggagaggt gcggcggcag ccaatcagag    660
cggcgcgctc cgaaagtttc cttttatggc gaggcggcgg cggcggcggc cctataaaaa    720
gcgaagcgcg cggcgggcgg gagcgggatc agccaccgcg gtggcggccc tagagtcgat    780
cgaggaactg aaaaaccaga aagttaactg gtaagtttag tctttttgtc ttttatttca    840
ggtcccggat ccggtggtgg tgcaaatcaa agaactgctc ctcagtggat gttgccttta    900
cttctaggcc tgtacggaag tgttacttct gctctaaaag ctgcggaatt gtacccgcgg    960
ccgatccacc ggggtaccaa gcttgccacc atggactgga cctggatcct gttcctggtg   1020
gccgccgcta caagagtgca cagcaatatc accaacctgt gccccttcgg cgaagtgttc   1080
aacgccacaa gattcgcctc tgtgtacgcc tggaacagga agcggatctc taactgcgtc   1140
gccgactaca gcgtgctgta caacagcgcc agcttctcca cctttaagtg ttacggcgtg   1200
tcccctacca agctgaacga cctgtgcttc accaacgtgt acgccgattc tttcgtgatc   1260
agaggcgacg aggtgcggca gatcgcccct ggccagacag gaaagatcgc tgattacaac   1320
tacaagctgc cagacgactt caccggatgt gtgatcgcct ggaatagcaa caacctggac   1380
agcaaggtgg gcggcaacta taactacctg tatagactgt tcagaaagtc caacctgaaa   1440
cctttcgaga gagatatcag caccgagatc taccaggccg gatctacccc atgtaatggc   1500
gtggaaggat ttaattgcta cttcccccctg cagagctacg gctttcagcc tacaaatggc   1560
gtgggctacc aaccttacag agtggtggtc ctgagcttcg agctgctgca cgcccctgct   1620
acagtgtgcg gccctaagaa aagcacaaac ctggtgaaga acaaatgcgt gaacttcaac   1680
ttcaacggcc tgaccggtac aggcgttctc accgagagca acaagaagtt cctgcccttc   1740
cagcagttcg gcagagacat tgctgacacc accgatgccg tgcgggaccc ccagaccctg   1800
gaaatcctgg atatcacacc ttgcagcttt ggctaggaat tccgctcgag ataatcaacc   1860
tctggattac aaaatttgtg aaagattgac tggtattctt aactatgttg ctccttttac   1920
gctatgtgga tacgctgctt taatgccttt gtatcatgct attgcttccc gtatggcttt   1980
cattttctcc tccttgtata aatcctggtt agttcttgcc acggcggaac tcatcgccgc   2040
ctgccttgcc cgctgctgga caggggctcg gctgttgggc actgacaatt ccgtggtgtt   2100
tatttgtgaa atttgtgatg ctattgcttt atttgtaacc atctagcttt atttgtgaaa   2160
tttgtgatgc tattgcttta tttgtaacca ttataagctg caataaacaa gttaacaaca   2220
acaattgcat tcattttatg tttcaggttc agggggagat gtgggaggtt ttttaaagcg   2280
gccgcaggaa cccctagtga tggagttggc cactccctct ctgcgcgctc gctcgctcac   2340
tgaggccggg cgaccaaagg tcgcccgacg cccgggcttt gcccgggcgg cctcagtgag   2400
cgagcgagcg cgcagctgcc tgcaggggcg cctgatgcgg tattttctcc ttacgcatct   2460
gtgcggtatt tcacaccgca tacgtcaaag caaccatagt acgcgccctg tagcggcgca   2520
ttaagcgcgg cgggtgtggt ggttacgcgc agcgtgaccg ctacacttgc cagcgcccta   2580
gcgcccgctc ctttcgcttt cttcccttcc tttctcgcca cgttcgccgg ctttccccgt   2640
```

```
caagctctaa atcgggggct ccctttaggg ttccgattta gtgctttacg gcacctcgac   2700

cccaaaaaac ttgatttggg tgatggttca cgtagtgggc catcgccctg atagacggtt   2760

tttcgccctt tgacgttgga gtccacgttc tttaatagtg gactcttgtt ccaaactgga   2820

acaacactca accctatctc gggctattct tttgatttat aagggatttt gccgatttcg   2880

gcctattggt taaaaaatga gctgatttaa caaaaattta acgcgaattt taacaaaata   2940

ttaacgttta caattttatg gtgcactctc agtacaatct gctctgatgc cgcatagtta   3000

agccagcccc gacacccgcc aacacccgct gacgcgccct gacgggcttg tctgctcccg   3060

gcatccgctt acagacaagc tgtgaccgtc tccgggagct gcatgtgtca gaggttttca   3120

ccgtcatcac cgaaacgcgc gagacgaaag ggcctcgtga tacgcctatt tttataggtt   3180

aatgtcatga taataatggt ttcttagacg tcaggtggca cttttcgggg aaatgtgcgc   3240

ggaaccccta tttgtttatt tttctaaata cattcaaata tgtatccgct catgagacaa   3300

taaccctgat aaatgcttca ataatattga aaaaggaaga gtatgagtat tcaacatttc   3360

cgtgtcgccc ttattccctt ttttgcggca ttttgccttc ctgtttttgc tcacccagaa   3420

acgctggtga aagtaaaaga tgctgaagat cagttgggtg cacgagtggg ttacatcgaa   3480

ctggatctca acagcggtaa gatccttgag agttttcgcc ccgaagaacg ttttccaatg   3540

atgagcactt ttaaagttct gctatgtggc gcggtattat cccgtattga cgccgggcaa   3600

gagcaactcg gtcgccgcat acactattct cagaatgact tggttgagta ctcaccagtc   3660

acagaaaagc atcttacgga tggcatgaca gtaagagaat tatgcagtgc tgccataacc   3720

atgagtgata acactgcggc caacttactt ctgacaacga tcggaggacc gaaggagcta   3780

accgcttttt tgcacaacat gggggatcat gtaactcgcc ttgatcgttg ggaaccggag   3840

ctgaatgaag ccataccaaa cgacgagcgt gacaccacga tgcctgtagc aatggcaaca   3900

acgttgcgca aactattaac tggcgaacta cttactctag cttcccggca acaattaata   3960

gactggatgg aggcggataa agttgcagga ccacttctgc gctcggccct tccggctggc   4020

tggtttattg ctgataaatc tggagccggt gagcgtgggt ctcgcggtat cattgcagca   4080

ctggggccag atggtaagcc ctcccgtatc gtagttatct acacgacggg gagtcaggca   4140

actatggatg aacgaaatag acagatcgct gagataggtg cctcactgat taagcattgg   4200

taactgtcag accaagttta ctcatatata ctttagattg atttaaaact tcatttttaa   4260

tttaaaagga tctaggtgaa gatccttttt gataatctca tgaccaaaat cccttaacgt   4320

gagttttcgt tccactgagc gtcagacccc gtagaaaaga tcaaaggatc ttcttgagat   4380

cctttttttc tgcgcgtaat ctgctgcttg caaacaaaaa aaccaccgct accagcggtg   4440

gtttgtttgc cggatcaaga gctaccaact ctttttccga aggtaactgg cttcagcaga   4500

gcgcagatac caaatactgt ccttctagtg tagccgtagt taggccacca cttcaagaac   4560

tctgtagcac cgcctacata cctcgctctg ctaatcctgt taccagtggc tgctgccagt   4620

ggcgataagt cgtgtcttac cgggttggac tcaagacgat agttaccgga taaggcgcag   4680

cggtcgggct gaacgggggg ttcgtgcaca cagcccagct tggagcgaac gacctacacc   4740

gaactgagat acctacagcg tgagctatga gaaagcgcca cgcttcccga agggagaaag   4800

gcggacaggt atccggtaag cggcagggtc ggaacaggag agcgcacgag ggagcttcca   4860

gggggaaacg cctggtatct ttatagtcct gtcgggtttc gccacctctg acttgagcgt   4920

cgatttttgt gatgctcgtc aggggggcgg agcctatgga aaaacgccag caacgcggcc   4980
```

-continued

```
tttttacggt tcctggcctt ttgctggcct tttgctcaca tgt                   5023


<210> SEQ ID NO 5
<211> LENGTH: 4903
<212> TYPE: DNA
<213> ORGANISM: Artificial Sequence
<220> FEATURE:
<223> OTHER INFORMATION: Synthetic

<400> SEQUENCE: 5

cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccattc ggtacaattc acgcgtcgac attgattatt gactagctct    180

ggtcgttaca taacttacgg taaatggccc gcctggctga ccgcccaacg acccccgccc    240

attgacgtca ataatgacgt atgttcccat agtaacgcca atagggactt tccattgacg    300

tcaatgggtg gagtatttac ggtaaactgc ccacttggca gtacatcaag tgtatcatat    360

gccaagtacg ccccctattg acgtcaatga cggtaaatgg cccgcctggc attatgccca    420

gtacatgacc ttatgggact ttcctacttg gcagtacatc tactcgaggc cacgttctgc    480

ttcactctcc ccatctcccc cccctcccca cccccaattt tgtatttatt tattttttaa    540

ttattttgtg cagcgatggg ggcggggggg gggggggggg gggcgcgcgc caggcggggc    600

ggggcggggc gaggggcggg gcggggcgag gcggagaggt gcggcggcag ccaatcagag    660

cggcgcgctc cgaaagtttc cttttatggc gaggcggcgg cggcggcggc cctataaaaa    720

gcgaagcgcg cggcgggcgg gagcgggatc agccaccgcg gtggcggccc tagagtcgat    780

cgaggaactg aaaaaccaga aagttaactg gtaagtttag tctttttgtc ttttatttca    840

ggtcccggat ccggtggtgg tgcaaatcaa agaactgctc ctcagtggat gttgccttta    900

cttctaggcc tgtacggaag tgttacttct gctctaaaag ctgcggaatt gtacccgcgg    960

ccgatccacc ggggtaccaa gcttgccacc atggactgga cctggatcct gttcctggtg   1020

gccgccgcta caagagtgca cagccgcgtg cagcccaccg agagcatcgt gcggtttcca   1080

aacatcacca atctctgtcc tttcggcgag gtctttaacg ccaccagatt cgccagcgtg   1140

tacgcctgga atagaaaaag aatcagcaat tgcgtggccg actacagcgt gctgtacaac   1200

tccgcctctt tcagcacatt caagtgctac ggcgtgtccc ctacaaagct gaacgacctg   1260

tgcttcacca acgtgtacgc tgatagcttc gtgattagag gagatgaggt gcggcagatc   1320

gctcctggcc agacaggcaa gatcgccgat tacaactaca agctgcctga cgacttcacc   1380

ggctgtgtga tcgcctggaa ctctaacaac ctggacagca aggtgggcgg aaattacaac   1440

tacctgtata gactgttcag aaagtccaac ctgaagccct tcgaacggga catctctaca   1500

gaaatctacc aggccggcag cacccccttgt aatggcgtgg aaggcttcaa ctgctacttc  1560

cccctgcaga gctacggctt tcagcctacc aacggcgttg gatatcaacc atacagagtg   1620

gtggtcctga gctttgagct gctgcacgcc cctgctacag tgtgcggccc caagaaaagc   1680

accaacctgg tgaagaacaa atgcgtgaac ttctaggaat tccgctcgag ataatcaacc   1740

tctggattac aaaatttgtg aaagattgac tggtattctt aactatgttg ctccttttac   1800

gctatgtgga tacgctgctt taatgccttt gtatcatgct attgcttccc gtatggcttt   1860

cattttctcc tccttgtata aatcctggtt agttcttgcc acggcggaac tcatcgccgc   1920

ctgccttgcc cgctgctgga caggggctcg gctgttgggc actgacaatt ccgtggtgtt   1980

tatttgtgaa atttgtgatg ctattgcttt atttgtaacc atctagcttt atttgtgaaa   2040
```

```
tttgtgatgc tattgcttta tttgtaacca ttataagctg caataaacaa gttaacaaca   2100
acaattgcat tcattttatg tttcaggttc agggggagat gtgggaggtt ttttaaagcg   2160
gccgcaggaa cccctagtga tggagttggc cactccctct ctgcgcgctc gctcgctcac   2220
tgaggccggg cgaccaaagg tcgcccgacg cccgggcttt gcccgggcgg cctcagtgag   2280
cgagcgagcg cgcagctgcc tgcaggggcg cctgatgcgg tattttctcc ttacgcatct   2340
gtgcggtatt tcacaccgca tacgtcaaag caaccatagt acgcgccctg tagcggcgca   2400
ttaagcgcgg cgggtgtggt ggttacgcgc agcgtgaccg ctacacttgc cagcgcccta   2460
gcgcccgctc ctttcgcttt cttcccttcc tttctcgcca cgttcgccgg ctttccccgt   2520
caagctctaa atcgggggct ccctttaggg ttccgattta gtgctttacg gcacctcgac   2580
cccaaaaaac ttgatttggg tgatggttca cgtagtgggc catcgccctg atagacggtt   2640
tttcgccctt tgacgttgga gtccacgttc tttaatagtg gactcttgtt ccaaactgga   2700
acaacactca accctatctc gggctattct tttgatttat aagggatttt gccgatttcg   2760
gcctattggt taaaaaatga gctgatttaa caaaaattta acgcgaattt taacaaaata   2820
ttaacgttta caattttatg gtgcactctc agtacaatct gctctgatgc cgcatagtta   2880
agccagcccc gacacccgcc aacacccgct gacgcgccct gacgggcttg tctgctcccg   2940
gcatccgctt acagacaagc tgtgaccgtc tccgggagct gcatgtgtca gaggttttca   3000
ccgtcatcac cgaaacgcgc gagacgaaag ggcctcgtga tacgcctatt tttataggtt   3060
aatgtcatga taataatggt ttcttagacg tcaggtggca cttttcgggg aaatgtgcgc   3120
ggaaccccta tttgtttatt tttctaaata cattcaaata tgtatccgct catgagacaa   3180
taaccctgat aaatgcttca ataatattga aaaaggaaga gtatgagtat tcaacatttc   3240
cgtgtcgccc ttattccctt ttttgcggca ttttgccttc ctgtttttgc tcacccagaa   3300
acgctggtga aagtaaaaga tgctgaagat cagttgggtg cacgagtggg ttacatcgaa   3360
ctggatctca acagcggtaa gatccttgag agttttcgcc ccgaagaacg ttttccaatg   3420
atgagcactt ttaaagttct gctatgtggc gcggtattat cccgtattga cgccgggcaa   3480
gagcaactcg gtcgccgcat acactattct cagaatgact tggttgagta ctcaccagtc   3540
acagaaaagc atcttacgga tggcatgaca gtaagagaat tatgcagtgc tgccataacc   3600
atgagtgata acactgcggc caacttactt ctgacaacga tcggaggacc gaaggagcta   3660
accgcttttt tgcacaacat gggggatcat gtaactcgcc ttgatcgttg ggaaccggag   3720
ctgaatgaag ccataccaaa cgacgagcgt gacaccacga tgcctgtagc aatggcaaca   3780
acgttgcgca aactattaac tggcgaacta cttactctag cttcccggca acaattaata   3840
gactggatgg aggcggataa agttgcagga ccacttctgc gctcggccct tccggctggc   3900
tggtttattg ctgataaatc tggagccggt gagcgtgggt ctcgcggtat cattgcagca   3960
ctggggccag atggtaagcc ctcccgtatc gtagttatct acacgacggg gagtcaggca   4020
actatggatg aacgaaatag acagatcgct gagataggtg cctcactgat taagcattgg   4080
taactgtcag accaagttta ctcatatata ctttagattg atttaaaact tcatttttaa   4140
tttaaaagga tctaggtgaa gatccttttt gataatctca tgaccaaaat cccttaacgt   4200
gagttttcgt tccactgagc gtcagacccc gtagaaaaga tcaaaggatc ttcttgagat   4260
cctttttttc tgcgcgtaat ctgctgcttg caaacaaaaa aaccaccgct accagcggtg   4320
gtttgtttgc cggatcaaga gctaccaact ctttttccga aggtaactgg cttcagcaga   4380
```

```
gcgcagatac caaatactgt ccttctagtg tagccgtagt taggccacca cttcaagaac   4440

tctgtagcac cgcctacata cctcgctctg ctaatcctgt taccagtggc tgctgccagt   4500

ggcgataagt cgtgtcttac cgggttggac tcaagacgat agttaccgga taaggcgcag   4560

cggtcgggct gaacgggggg ttcgtgcaca cagcccagct tggagcgaac gacctacacc   4620

gaactgagat acctacagcg tgagctatga gaaagcgcca cgcttcccga agggagaaag   4680

gcggacaggt atccggtaag cggcagggtc ggaacaggag agcgcacgag ggagcttcca   4740

gggggaaacg cctggtatct ttatagtcct gtcgggtttc gccacctctg acttgagcgt   4800

cgatttttgt gatgctcgtc aggggggcgg agcctatgga aaaacgccag caacgcggcc   4860

tttttacggt tcctggcctt ttgctggcct tttgctcaca tgt                     4903
```

<210> SEQ ID NO 6
<211> LENGTH: 29903
<212> TYPE: DNA
<213> ORGANISM: SARS-COV-2(Coronavirus)

<400> SEQUENCE: 6

```
attaaaggtt tataccttcc caggtaacaa accaaccaac tttcgatctc ttgtagatct     60

gttctctaaa cgaactttaa aatctgtgtg gctgtcactc ggctgcatgc ttagtgcact    120

cacgcagtat aattaataac taattactgt cgttgacagg acacgagtaa ctcgtctatc    180

ttctgcaggc tgcttacggt ttcgtccgtg ttgcagccga tcatcagcac atctaggttt    240

cgtccgggtg tgaccgaaag gtaagatgga gagccttgtc cctggtttca acgagaaaac    300

acacgtccaa ctcagtttgc ctgttttaca ggttcgcgac gtgctcgtac gtggctttgg    360

agactccgtg gaggaggtct tatcagaggc acgtcaacat cttaaagatg gcacttgtgg    420

cttagtagaa gttgaaaaag gcgttttgcc tcaacttgaa cagccctatg tgttcatcaa    480

acgttcggat gctcgaactg cacctcatgg tcatgttatg gttgagctgg tagcagaact    540

cgaaggcatt cagtacggtc gtagtggtga gacacttggt gtccttgtcc ctcatgtggg    600

cgaaatacca gtggcttacc gcaaggttct tcttcgtaag aacggtaata aaggagctgg    660

tggccatagt tacggcgccg atctaaagtc atttgactta ggcgacgagc ttggcactga    720

tccttatgaa gattttcaag aaaactggaa cactaaacat agcagtggtg ttacccgtga    780

actcatgcgt gagcttaacg gaggggcata cactcgctat gtcgataaca acttctgtgg    840

ccctgatggc taccctcttg agtgcattaa agaccttcta gcacgtgctg gtaaagcttc    900

atgcactttg tccgaacaac tggactttat tgacactaag aggggtgtat actgctgccg    960

tgaacatgag catgaaattg cttggtacac ggaacgttct gaaaagagct atgaattgca   1020

gacacctttt gaaattaaat tggcaaagaa atttgacacc ttcaatgggg aatgtccaaa   1080

ttttgtattt cccttaaatt ccataatcaa gactattcaa ccaagggttg aaaagaaaaa   1140

gcttgatggc tttatgggta gaattcgatc tgtctatcca gttgcgtcac caaatgaatg   1200

caaccaaatg tgcctttcaa ctctcatgaa gtgtgatcat tgtggtgaaa cttcatggca   1260

gacgggcgat tttgttaaag ccacttgcga attttgtggc actgagaatt tgactaaaga   1320

aggtgccact acttgtggtt acttacccca aaatgctgtt gttaaaattt attgtccagc   1380

atgtcacaat tcagaagtag gacctgagca tagtcttgcc gaataccata atgaatctgg   1440

cttgaaaacc attcttcgta agggtggtcg cactattgcc tttggaggct gtgtgttctc   1500

ttatgttggt tgccataaca agtgtgccta ttgggttcca cgtgctagcg ctaacatagg   1560

ttgtaaccat acaggtgttg ttggagaagg ttccgaaggt cttaatgaca accttcttga   1620
```

```
aatactccaa aaagagaaag tcaacatcaa tattgttggt gactttaaac ttaatgaaga   1680
gatcgccatt attttggcat ctttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
agaaggtgat tgtgaagaag aagagtttga gccatcaact caatatgagt atggtactga   3120
agatgattac caaggtaaac ctttggaatt tggtgccact tctgctgctc ttcaacctga   3180
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
agagatggaa cttacaccag ttgttcagac tattgaagtg aatagtttta gtggttattt   3360
aaaacttact gacaatgtat acattaaaaa tgcagacatt gtggaagaag ctaaaaaggt   3420
aaaaccaaca gtggttgtta atgcagccaa tgtttacctt aaacatggag gaggtgttgc   3480
aggagcctta aataaggcta ctaacaatgc catgcaagtt gaatctgatg attacatagc   3540
tactaatgga ccacttaaag tgggtggtag ttgtgtttta agcggacaca atcttgctaa   3600
acactgtctt catgttgtcg gcccaaatgt taacaaaggt gaagacattc aacttcttaa   3660
gagtgcttat gaaaatttta atcagcacga agttctactt gcaccattat tatcagctgg   3720
tatttttggt gctgacccta tacattcttt aagagtttgt gtagatactg ttcgcacaaa   3780
tgtctactta gctgtctttg ataaaaatct ctatgacaaa cttgtttcaa gctttttgga   3840
aatgaagagt gaaaagcaag ttgaacaaaa gatcgctgag attcctaaag aggaagttaa   3900
gccatttata actgaaagta aaccttcagt tgaacagaga aaacaagatg ataagaaaat   3960
```

-continued

```
caaagcttgt gttgaagaag ttacaacaac tctggaagaa actaagttcc tcacagaaaa   4020
cttgttactt tatattgaca ttaatggcaa tcttcatcca gattctgcca ctcttgttag   4080
tgacattgac atcactttct taaagaaaga tgctccatat atagtgggtg atgttgttca   4140
agagggtgtt ttaactgctg tggttatacc tactaaaaag gctggtggca ctactgaaat   4200
gctagcgaaa gctttgagaa aagtgccaac agacaattat ataaccactt acccgggtca   4260
gggtttaaat ggttacactg tagaggaggc aaagacagtg cttaaaaagt gtaaaagtgc   4320
cttttacatt ctaccatcta ttatctctaa tgagaagcaa gaaattcttg gaactgtttc   4380
ttggaatttg cgagaaatgc ttgcacatgc agaagaaaca cgcaaattaa tgcctgtctg   4440
tgtggaaact aaagccatag tttcaactat acagcgtaaa tataagggta ttaaaataca   4500
agagggtgtg gttgattatg gtgctagatt ttacttttac accagtaaaa caactgtagc   4560
gtcacttatc aacacactta acgatctaaa tgaaactctt gttacaatgc cacttggcta   4620
tgtaacacat ggcttaaatt tggaagaagc tgctcggtat atgagatctc tcaaagtgcc   4680
agctacagtt tctgtttctt cacctgatgc tgttacagcg tataatggtt atcttacttc   4740
ttcttctaaa acacctgaag aacattttat tgaaaccatc tcacttgctg gttcctataa   4800
agattggtcc tattctggac aatctacaca actaggtata gaatttctta agagaggtga   4860
taaaagtgta tattacacta gtaatcctac cacattccac ctagatggtg aagttatcac   4920
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc cacaagttaa tggtttaact tctattaaat gggcagataa   5280
caactgttat cttgccactg cattgttaac actccaacaa atagagttga agtttaatcc   5340
acctgctcta caagatgctt attacagagc aagggctggt gaagctgcta acttttgtgc   5400
acttatctta gcctactgta ataagacagt aggtgagtta ggtgatgtta gagaaacaat   5460
gagttacttg tttcaacatg ccaatttaga ttcttgcaaa agagtcttga acgtggtgtg   5520
taaaacttgt ggacaacagc agacaaccct taagggtgta gaagctgtta tgtacatggg   5580
cacactttct tatgaacaat ttaagaaagg tgttcagata ccttgtacgt gtggtaaaca   5640
agctacaaaa tatctagtac aacaggagtc accttttgtt atgatgtcag caccacctgc   5700
tcagtatgaa cttaagcatg gtacatttac ttgtgctagt gagtacactg gtaattacca   5760
gtgtggtcac tataaacata taacttctaa agaaactttg tattgcatag acggtgcttt   5820
acttacaaag tcctcagaat acaaaggtcc tattacggat gttttctaca aagaaaacag   5880
ttacacaaca accataaaac cagttactta taaattggat ggtgttgttt gtacagaaat   5940
tgaccctaag ttggacaatt attataagaa agacaattct tatttcacag agcaaccaat   6000
tgatcttgta ccaaaccaac catatccaaa cgcaagcttc gataatttta agtttgtatg   6060
tgataatatc aaatttgctg atgatttaaa ccagttaact ggttataaga aacctgcttc   6120
aagagagctt aaagttacat ttttccctga cttaaatggt gatgtggtgg ctattgatta   6180
taaacactac acaccctctt ttaagaaagg agctaaattg ttacataaac ctattgtttg   6240
gcatgttaac aatgcaacta ataaagccac gtataaacca aatacctggt gtatacgttg   6300
tctttggagc acaaaaccag ttgaaacatc aaattcgttt gatgtactga agtcagagga   6360
```

```
cgcgcaggga atggataatc ttgcctgcga agatctaaaa ccagtctctg aagaagtagt   6420
ggaaaatcct accatacaga aagacgttct tgagtgtaat gtgaaaacta ccgaagttgt   6480
aggagacatt atacttaaac cagcaaataa tagtttaaaa attacagaag aggttggcca   6540
cacagatcta atggctgctt atgtagacaa ttctagtctt actattaaga aacctaatga   6600
attatctaga gtattaggtt tgaaaaccct tgctactcat ggtttagctg ctgttaatag   6660
tgtcccttgg gatactatag ctaattatgc taagcctttt cttaacaaag ttgttagtac   6720
aactactaac atagttacac ggtgtttaaa ccgtgtttgt actaattata tgccttattt   6780
ctttacttta ttgctacaat tgtgtacttt tactagaagt acaaattcta gaattaaagc   6840
atctatgccg actactatag caaagaatac tgttaagagt gtcggtaaat tttgtctaga   6900
ggcttcattt aattatttga agtcacctaa tttttctaaa ctgataaata ttataatttg   6960
gtttttacta ttaagtgttt gcctaggttc tttaatctac tcaaccgctg ctttaggtgt   7020
tttaatgtct aatttaggca tgccttctta ctgtactggt tacagagaag gctatttgaa   7080
ctctactaat gtcactattg caacctactg tactggttct ataccttgta gtgtttgtct   7140
tagtggttta gattctttag acacctatcc ttctttagaa actatacaaa ttaccatttc   7200
atcttttaaa tgggatttaa ctgcttttgg cttagttgca gagtggtttt tggcatatat   7260
tcttttcact aggtttttct atgtacttgg attggctgca atcatgcaat tgtttttcag   7320
ctattttgca gtacatttta ttagtaattc ttggcttatg tggttaataa ttaatcttgt   7380
acaaatggcc ccgatttcag ctatggttag aatgtacatc ttctttgcat cattttatta   7440
tgtatggaaa agttatgtgc atgttgtaga cggttgtaat tcatcaactt gtatgatgtg   7500
ttacaaacgt aatagagcaa caagagtcga atgtacaact attgttaatg gtgttagaag   7560
gtccttttat gtctatgcta atggaggtaa aggcttttgc aaactacaca attggaattg   7620
tgttaattgt gatacattct gtgctggtag tacatttatt agtgatgaag ttgcgagaga   7680
cttgtcacta cagtttaaaa gaccaataaa tcctactgac cagtcttctt acatcgttga   7740
tagtgttaca gtgaagaatg gttccatcca tctttacttt gataaagctg gtcaaaagac   7800
ttatgaaaga cattctctct ctcattttgt taacttagac aacctgagag ctaataacac   7860
taaaggttca ttgcctatta atgttatagt ttttgatggt aaatcaaaat gtgaagaatc   7920
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta aagatgttgt   8220
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
tgctaaaaag aataacttac cttttaagtt gacatgtgca actactagac aagttgttaa   8520
tgttgtaaca acaaagatag cacttaaggg tggtaaaatt gttaataatt ggttgaagca   8580
gttaattaaa gttacacttg tgttcctttt tgttgctgct attttctatt taataacacc   8640
tgttcatgtc atgtctaaac atactgactt ttcaagtgaa atcataggat acaaggctat   8700
```

```
tgatggtggt gtcactcgtg acatagcatc tacagatact tgttttgcta acaaacatgc   8760

tgattttgac acatggttta gccagcgtgg tggtagttat actaatgaca aagcttgccc   8820

attgattgct gcagtcataa caagagaagt gggttttgtc gtgcctggtt tgcctggcac   8880

gatattacgc acaactaatg gtgacttttt gcatttctta cctagagttt ttagtgcagt   8940

tggtaacatc tgttacacac catcaaaact tatagagtac actgactttg caacatcagc   9000

ttgtgttttg gctgctgaat gtacaatttt taaagatgct tctggtaagc cagtaccata   9060

ttgttatgat accaatgtac tagaaggttc tgttgcttat gaaagtttac gccctgacac   9120

acgttatgtg ctcatggatg gctctattat tcaatttcct aacacctacc ttgaaggttc   9180

tgttagagtg gtaacaactt ttgattctga gtactgtagg cacggcactt gtgaaagatc   9240

agaagctggt gtttgtgtat ctactagtgg tagatgggta cttaacaatg attattacag   9300

atctttacca ggagttttct gtggtgtaga tgctgtaaat ttacttacta atatgtttac   9360

accactaatt caacctattg gtgctttgga catatcagca tctatagtag ctggtggtat   9420

tgtagctatc gtagtaacat gccttgccta ctattttatg aggtttagaa gagcttttgg   9480

tgaatacagt catgtagttg cctttaatac tttactattc cttatgtcat tcactgtact   9540

ctgtttaaca ccagtttact cattcttacc tggtgtttat tctgttattt acttgtactt   9600

gacattttat cttactaatg atgtttcttt tttagcacat attcagtgga tggttatgtt   9660

cacaccttta gtacctttct ggataacaat tgcttatatc atttgtattt ccacaaagca   9720

tttctattgg ttctttagta attacctaaa gagacgtgta gtctttaatg gtgtttcctt   9780

tagtactttt gaagaagctg cgctgtgcac ctttttgtta aataaagaaa tgtatctaaa   9840

gttgcgtagt gatgtgctat tacctcttac gcaatataat agatacttag ctctttataa   9900

taagtacaag tattttagtg gagcaatgga tacaactagc tacagagaag ctgcttgttg   9960

tcatctcgca aaggctctca atgacttcag taactcaggt tctgatgttc tttaccaacc  10020

accacaaacc tctatcacct cagctgtttt gcagagtggt tttagaaaaa tggcattccc  10080

atctggtaaa gttgagggtt gtatggtaca agtaacttgt ggtacaacta cacttaacgg  10140

tctttggctt gatgacgtag tttactgtcc aagacatgtg atctgcacct ctgaagacat  10200

gcttaaccct aattatgaag atttactcat tcgtaagtct aatcataatt tcttggtaca  10260

ggctggtaat gttcaactca gggttattgg acattctatg caaaattgtg tacttaagct  10320

taaggttgat acagccaatc ctaagacacc taagtataag tttgttcgca ttcaaccagg  10380

acagactttt tcagtgttag cttgttacaa tggttcacca tctggtgttt accaatgtgc  10440

tatgaggccc aatttcacta ttaagggttc attccttaat ggttcatgtg gtagtgttgg  10500

ttttaacata gattatgact gtgtctcttt ttgttacatg caccatatgg aattaccaac  10560

tggagttcat gctggcacag acttagaagg taacttttat ggaccttttg ttgacaggca  10620

aacagcacaa gcagctggta cggacacaac tattacagtt aatgttttag cttggttgta  10680

cgctgctgtt ataaatggag acaggtggtt tctcaatcga tttaccacaa ctcttaatga  10740

ctttaacctt gtggctatga agtacaatta tgaacctcta acacaagacc atgttgacat  10800

actaggacct ctttctgctc aaactggaat tgccgtttta gatatgtgtg cttcattaaa  10860

agaattactg caaaatggta tgaatggacg taccatattg ggtagtgctt tattagaaga  10920

tgaatttaca ccttttgatg ttgttagaca atgctcaggt gttactttcc aaagtgcagt  10980

gaaaagaaca atcaagggta cacaccactg gttgttactc acaattttga cttcactttt  11040

agttttagtc cagagtactc aatggtcttt gttctttttt ttgtatgaaa atgccttttt  11100
```

```
acctttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
```

-continued

```
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
```

-continued

```
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
```

-continued

```
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtctttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcacctttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
```

```
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attacccccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
```

-continued

```
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt taataggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaatttttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgatttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
aatcattact acagacaaca catttgtgtc tggtaactgt gatgttgtaa taggaattgt  24960
caacaacaca gtttatgatc ctttgcaacc tgaattagac tcattcaagg aggagttaga  25020
taaatatttt aagaatcata catcaccaga tgttgattta ggtgacatct ctggcattaa  25080
tgcttcagtt gtaaacattc aaaaagaaat tgaccgcctc aatgaggttg ccaagaattt  25140
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
```

```
ctgcaaattt gatgaagacg actctgagcc agtgctcaaa ggagtcaaat tacattacac  25380
ataaacgaac ttatggattt gtttatgaga atcttcacaa ttggaactgt aactttgaag  25440
caaggtgaaa tcaaggatgc tactccttca gattttgttc gcgctactgc aacgataccg  25500
atacaagcct cactcccttt cggatggctt attgttggcg ttgcacttct tgctgttttt  25560
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc cccttttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtta  26280
atagttaata gcgtacttct ttttcttgct ttcgtggtat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
gaagagcaac caatggagat tgattaaacg aacatgaaaa ttattctttt cttggcactg  27420
ataacactcg ctacttgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
```

```
caagaggaag ttcaagaact ttactctcca atttttctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgaaat  27900
ttcttgtttt cttaggaatc atcacaactg tagctgcatt tcaccaagaa tgtagtttac  27960
agtcatgtac tcaacatcaa ccatatgtag ttgatgaccc gtgtcctatt cacttctatt  28020
ctaaatggta tattagagta ggagctagaa aatcagcacc tttaattgaa ttgtgcgtgg  28080
atgaggctgg ttctaaatca cccattcagt acatcgatat cggtaattat acagtttcct  28140
gtttaccttt tacaattaat tgccaggaac ctaaattggg tagtcttgta gtgcgttgtt  28200
cgttctatga agacttttta gagtatcatg acgttcgtgt tgttttagat ttcatctaaa  28260
cgaacaaact aaaatgtctg ataatggacc ccaaaatcag cgaaatgcac cccgcattac  28320
gtttggtgga ccctcagatt caactggcag taaccagaat ggagaacgca gtggggcgcg  28380
atcaaaacaa cgtcggcccc aaggtttacc caataatact gcgtcttggt tcaccgctct  28440
cactcaacat ggcaaggaag accttaaatt ccctcgagga caaggcgttc caattaacac  28500
caatagcagt ccagatgacc aaattggcta ctaccgaaga gctaccagac gaattcgtgg  28560
tggtgacggt aaaatgaaag atctcagtcc aagatggtat ttctactacc taggaactgg  28620
gccagaagct ggacttccct atggtgctaa caaagacggc atcatatggg ttgcaactga  28680
gggagccttg aatacaccaa aagatcacat tggcacccgc aatcctgcta acaatgctgc  28740
aatcgtgcta caacttcctc aaggaacaac attgccaaaa ggcttctacg cagaagggag  28800
cagaggcggc agtcaagcct cttctcgttc ctcatcacgt agtcgcaaca gttcaagaaa  28860
ttcaactcca ggcagcagta ggggaacttc tcctgctaga atggctggca atggcggtga  28920
tgctgctctt gctttgctgc tgcttgacag attgaaccag cttgagagca aaatgtctgg  28980
taaaggccaa caacaacaag gccaaactgt cactaagaaa tctgctgctg aggcttctaa  29040
gaagcctcgg caaaaacgta ctgccactaa agcatacaat gtaacacaag ctttcggcag  29100
acgtggtcca gaacaaaccc aaggaaattt tggggaccag gaactaatca gacaaggaac  29160
tgattacaaa cattggccgc aaattgcaca atttgccccc agcgcttcag cgttcttcgg  29220
aatgtcgcgc attggcatgg aagtcacacc ttcgggaacg tggttgacct acacaggtgc  29280
catcaaattg gatgacaaag atccaaattt caaagatcaa gtcattttgc tgaataagca  29340
tattgacgca tacaaaacat tcccaccaac agagcctaaa aaggacaaaa agaagaaggc  29400
tgatgaaact caagccttac cgcagagaca gaagaaacag caaactgtga ctcttcttcc  29460
tgctgcagat ttggatgatt tctccaaaca attgcaacaa tccatgagca gtgctgactc  29520
aactcaggcc taaactcatg cagaccacac aaggcagatg ggctatataa acgttttcgc  29580
ttttccgttt acgatatata gtctactctt gtgcagaatg aattctcgta actacatagc  29640
acaagtagat gtagttaact ttaatctcac atagcaatct ttaatcagtg tgtaacatta  29700
gggaggactt gaaagagcca ccacattttc accgaggcca cgcggagtac gatcgagtgt  29760
acagtgaaca atgctaggga gagctgccta tatggaagag ccctaatgtg taaaattaat  29820
tttagtagtg ctatccccat gtgattttaa tagcttctta ggagaatgac aaaaaaaaaa  29880
aaaaaaaaaa aaaaaaaaaa aaa                                         29903
```

SARS-COV-2 ANTIGEN POLYPEPTIDE, RECOMBINANT ADENO-ASSOCIATED VIRUS EXPRESSING THE POLYPEPTIDE, AND VACCINE CONTAINING THE VIRUS

CROSS-REFERENCE TO RELATED APPLICATIONS

The present application is a Continuation-In-Part Application of PCT application No. PCT/CN2020/127311 filed on Nov. 7, 2020, which claims the benefit of Chinese Patent Application No. 202010392553.1 filed on May 11, 2020, the contents of which are hereby incorporated by reference.

REFERENCE TO SEQUENCE LISTING

A Sequence Listing is submitted as an ASCII formatted text file via EFS-Web, with a file name of "Sequence_Listing_SCH-21027-USPT.TXT", a creation date of May 20, 2021, and a size of 55,731 bytes. The Sequence Listing filed via. EFS-Web is part of the specification and is incorporated in its entirety by reference herein.

TECHNICAL FIELD

The present disclosure relates to the field of biotechnology, in particular, to a SARS-COV-2 antigen polypeptide, a recombinant adeno-associated virus expressing the polypeptide, and a vaccine containing the virus.

BACKGROUND

Coronaviruses belong to a large class of RNA viruses that exists widely in nature and can only infect vertebrates. In humans, coronaviruses can cause severe respiratory illnesses such as colds, severe acute respiratory syndrome (SARS) and Middle East respiratory syndrome (MERS).

Since the end of 2019, a new type of coronavirus, severe acute respiratory syndrome coronavirus 2 (SARS-COV-2), has caused a global pandemic of novel coronavirus pneumonia (COVID-19). SARS-COV-2 is highly latent and contagious. It causes not only asymptomatic infection, but also viral pneumonia, severe respiratory syndrome, renal failure, and death. Therefore, the development of a vaccine against COVID-19 is extremely important and urgent.

The SARS-COV-2 spike glycoprotein invades the body by binding to the angiotensin-converting enzyme 2 (ACE2) receptor on a cell membrane in the human body, hence the spike glycoprotein is a key target for vaccine development.

Wild-type adeno-associated virus (AAV) is a DNA virus with a diameter of about 22 nm and is not pathogenic to humans. The recombinant AAV obtained by genetic engineering of wild-type AAV has become a safe and effective delivery vector in gene therapy. At present, a number of gene drugs based on AAV vectors are commercially available abroad. AAV vectors are widely used in the development of vaccines, tumor drugs, and genetic disease drugs. The advantages of using AAV vectors to deliver antigen genes are that AAV vectors have very low auto-immunogenicity and genotoxicity; they could be highly efficiently delivered and they maintain long-term expression. AAV vector vaccines can be used to induce the production of antibodies by an endogenous antigen, and the production of antibodies is continuous and stable.

SUMMARY OF THE DISCLOSURE

The primary objective of the present disclosure is to provide a novel coronavirus (SARS-COV-2) antigen polypeptide.

Another objective of the present disclosure is to provide a recombinant adeno-associated virus expressing the antigen polypeptide.

Yet another objective of the present disclosure is to provide a COVID-19 vaccine prepared with the aforementioned recombinant adeno-associated virus.

An objective of the present disclosure is achieved by the following technical solutions:

A novel coronavirus (SARS-COV-2) antigen polypeptide, wherein an amino acid sequence of the antigen polypeptide is one of the following:

a) the sequence of amino acids 331-583 encoded by the gene sequence of SARS-COV-2 (SEQ ID NO: 6, GenBank accession no. NC_045512.2) is predicted to be a spike protein receptor domain, which is a target for inducing antibody production and preparing vaccine;
b) SEQ ID NO: 1 produced by attaching an additional amino acid sequence set forth in SEQ ID NO: 3 at the C-terminus of sequence a); this was to enrich the cysteine from the original sequence in the C-terminal to facilitate antigen aggregation;
c) SEQ ID NO: 2; the sequence of amino acids 319-541 encoded by the gene sequence of SARS-COV-2 (SEQ ID NO: 6, GenBank accession no. NC_045512.2) is predicted to be a spike protein receptor domain, which is a target for inducing antibody production and preparing vaccine;
d) an amino acid sequence having at least 90% sequence identity/similarity to a), b), or c); preferably, an amino acid sequence having 95%, 98% sequence identity/similarity to a) or b).

An expression vector of the aforementioned antigen peptide, comprising an adeno-associated virus inverted terminal repeat sequence (ITR sequence), a nucleotide sequence encoding a signal peptide, and a nucleotide sequence encoding the antigen peptide.

The expression vector also comprises an essential expression regulatory element, such as a promoter sequence, an upstream regulatory region, a coding region, a transcription regulatory element, a terminator, among others.

The nucleotide sequence encoding the signal peptide is optimized with human codons.

The inverted terminal repeat sequence is from adeno-associated virus (AAV) serotype 2.

The signal peptide is preferably an IgE signal peptide.

In another aspect of the disclosure, the application provides a method for preparing the recombinant adeno-associated virus, wherein the method comprises co-incubating pHelper, pRep2Cap5, and the expression vector, transfecting a cell in the presence of polyethyleneimine as a transfection reagent; culturing the cell, then collecting the cell by centrifugation, performing lysis and purification to obtain a purified liquid comprising the recombinant adeno-associated virus.

The pRep2Cap5 corresponds to serotype AAV5.

rAAV vectors can be produced by methods known to those skilled in the art. Those skilled in the art can use a well-known method based on HEK293 three-plasmid system to produce rAAV vectors, for example, as disclosed in Chinese invention patent ZL201710553164.0.

Those skilled in the art can also construct expression plasmids and serotype plasmids based on an insect system of an SF9 cell line to produce rAAVs, for example, as disclosed in Chinese patent publication CN108699567A. In addition, there are herpes-virus-based or adenovirus-based packaging systems, etc.

After rAAVs are produced, they can be purified from host cells by a variety of conventional purification methods such as physical lysis, chemical lysis, filtration and clarification, tangential flow ultrafiltration, column chromatography, CsCl gradient centrifugation, and iodixanol centrifugation. A detailed description of the purification methods above can be found in Nass S, Mattingly M, Woodcock D, et al. "Universal Method for the Purification of Recombinant AAV Vectors of Differing Serotypes", [J]. Molecular therapy. Methods & clinical development, 2018: 33-46.

The recombinant adeno-associated virus above can be used to prepare a vaccine for COVID-19.

The vaccine comprises a pharmaceutically acceptable diluent and/or a pharmaceutically acceptable excipient.

The vaccine can be prepared as injections and nasal sprays for intramuscular injection and intranasal spray immunization.

In another aspect, the disclosure provides a method of eliciting a protective immune response in a subject, wherein the method comprises administering to the subject a prophylactically or therapeutically effective dose of the vaccine.

The beneficial effects of the present disclosure are as follows:

1. Among the multiple specific antigenic determinants carried by protein macromolecular antigens, only a small number of antigenic sites contribute to the protective immune response. Immunogenicity depends on the properties of the substance itself, such as molecular weight, chemical properties, molecular structure, and molecular conformation. The SARS-COV-2 antigen polypeptide sequence predicted in the present disclosure has the following advantages as illustrated by experiments: a. compared with an intact S protein or the Si subunit as an antigen, a truncated domain sequence has higher specificity as a result of a shorter sequence, a smaller molecular weight, and a more defined structure; b. a serum antibody neutralization test showed that the antigen polypeptide of the present disclosure has high immunogenicity and can produce powerful protective neutralizing antibodies; c. for the first time, it is reported that the SARS-COV-2 antigen polypeptide nucleic acid sequence is delivered in the AAV5 recombinant adeno-associated virus by intramuscular injection, and the antigen sequence is expressed effectively and continuously.

2. The rAAV composition of the present disclosure is delivered and expressed in vivo to produce a fusion antigen polypeptide, induces the production of serum neutralizing antibodies, which have a neutralizing titer to the novel SARS-COV-2 coronavirus and are expressed continuously; the rAAV composition can be used to immunize humans against the novel coronavirus pneumonia COVID-19.

BRIEF DESCRIPTION OF THE DRAWINGS

FIG. 3A shows the effect on IgM antibody expression, FIG. 3B shows the effect on IgG antibody expression.

FIG. 5A shows the effect on IgM antibody expression, FIG. 5B shows the effect on IgG antibody expression.

EMBODIMENTS

Figure 1:
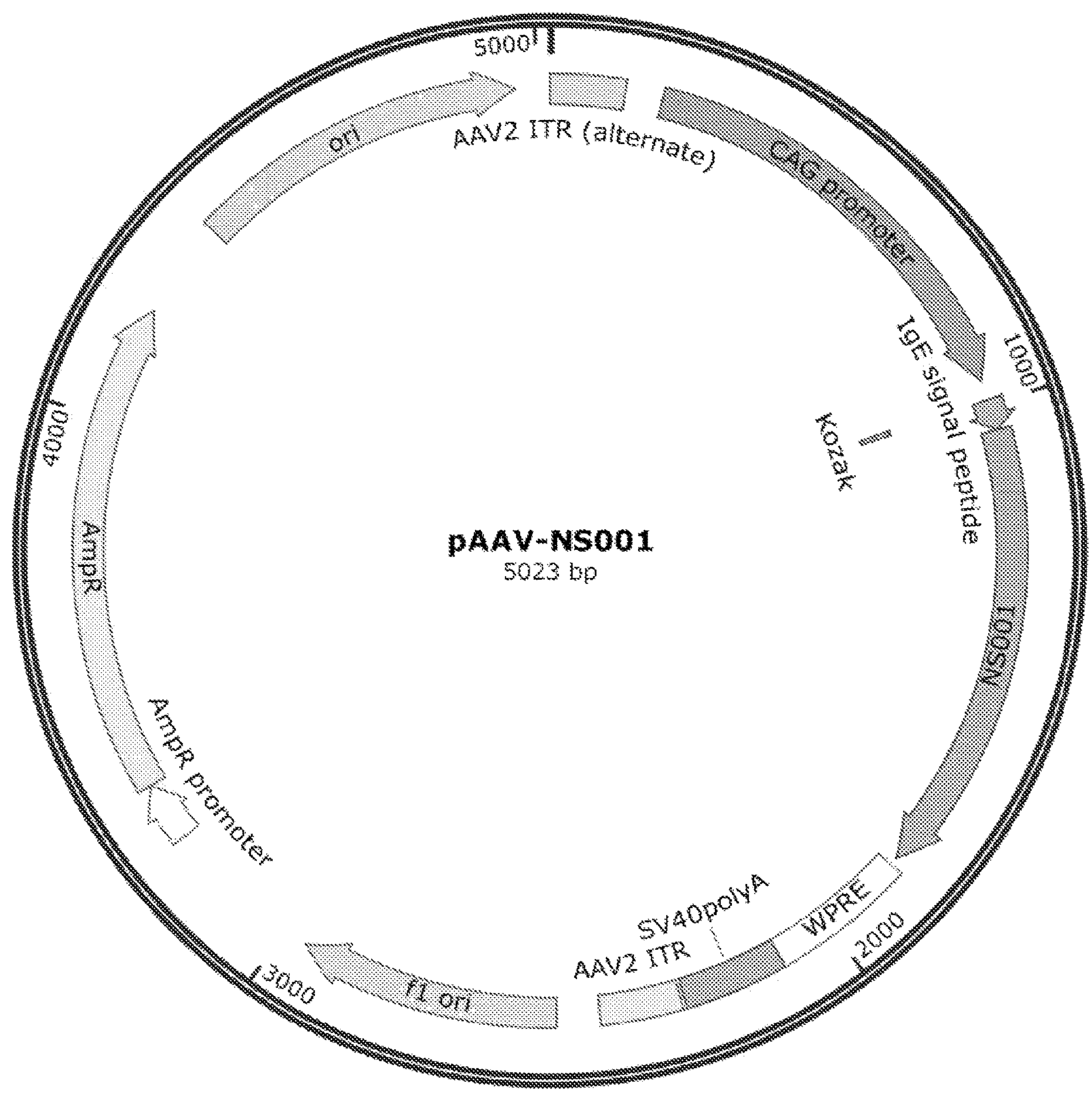
FIG. 1 is a schematic diagram of the completed vector map of pAAV-NS001; the key elements in the schematic diagram are described as follows: ITR refers to the inverted terminal repeat sequence of AAV2; CAG promoter refers to a combination of strong promoters, including cytomegalovirus (CMV) enhancer, chicken beta-actin promoter, and rabbit beta-globin splice acceptor; NS001 refers to the sequence set forth in SEQ ID NO: 1; WPRE is woodchuck hepatitis virus post-transcriptional regulatory element; SV40 PolyA is the polyadenylic acid sequence of monkey vacuolar virus 40 (SV40).

The present disclosure will be further described below in combination with specific examples and accompanying drawings, but the embodiments of the present disclosure are not limited thereto.

In the description of the disclosure, the following terms will be used, and a brief description of the terms is provided below.

S protein, also known as spike protein, is a capsid surface glycoprotein of a coronavirus. Novel coronavirus SARS-COV-2 binds to the human ACE2 receptor through the S protein and invades cells. A truncated S protein as an antigen is obtained by predicting and intercepting part region of the S protein.

A vector is a delivery vehicle or element for a genetic material. Examples of a vector include a plasmid, a virus, a virus-like particle, and a bacteriophage. The vector is often referred to as "cloning vector", "expression vector" or "backbone vector", and "viral vector" in different applications or scenarios.

An "rAAV vector" refers to a recombinant non-replicating adeno-associated virus. The rAAV vector includes a serotype capsid protein and encapsulates a recombinant genome. The genome includes functional 5' and 3' inverted terminal repeats sequences (ITR sequences). The ITR sequences are flanked by exogenous nucleotide sequences that replaced rep or cap genes found in wild-type AAVs. ITR sequences provide functional rescue, replication, and packaging to rAAVs. In some examples, the ITR sequences are from AAV2. Exogenous nucleotide sequences usually consist of a series of expression regulatory elements and coding regions.

An AAV serotype plasmid pREPCAP includes two open reading frames (ORFs) that encode the expression products of Rep and Cap. Cap refers to a capsid protein of AAV familiar to those skilled in the art. Cap encodes functional proteins such as capsid proteins VP1, VP2, VP3, and AAP. AAVs of different serotypes have different capsid protein sequences.

An AAV helper plasmid pHelper usually contains coding regions such as adeno-associated virus VA RNA, E4 ORF6, E2A, and E1B, which provide functions necessary for AAV replication.

Expression regulatory elements are generally a collection of promoter sequences, upstream regulatory regions, coding regions, and transcriptional regulatory elements, which jointly realize replication, transcription and translation of coding region sequences in receptor cells. A promoter is a DNA sequence that is recognized and bound by RNA polymerase, and initiates transcription. The promoter contains conserved sequences required for RNA polymerase specific binding and transcription initiation, most of which are located upstream of the transcription initiation point of structural genes; the promoter itself is not transcribed. In some cases, a CAG promoter is selected as the promoter sequence. Suitable promoters also include promoters known to those skilled in the art, such as human cytomegalovirus (CMV) promoter, ubiquitin C promoter (UbC), and EF1α promoter. Optionally, promoters can be selected to regulate the expression of mRNA transcription. In some cases, SV40 polyA is selected as a transcriptional terminator. Suitable polyA sequences include but are not limited to SV40 polyA, BGH polyA, and synthetic polyA, etc. known in the art. Some examples also include transcription-enhancing regulatory elements, such as woodchuck hepatitis virus post-transcriptional regulatory elements (WPREs) and sequences that increase translation efficiency (Kozak sequences).

In the following examples, experiments of which conditions are not specified are usually carried out in conventional conditions, for example, as described in Sambrook et al., "Molecular Cloning: a Laboratory Manual" (New York: Cold Spring Harbor Laboratory Press, 1989), or according to the manufacturer's protocol.

The materials used in the examples are commercially available unless otherwise specified.

Example 1 Construction of AAV Expression Vector Plasmid pAAV-NS001

The gene sequence of SARS-COV-2 (SEQ ID NO: 6, GenBank accession no. NC_045512.2) was NCBI acquired through the database. Conserved domains within the gene sequence were predicted by NCBI Conserved Domain Search.

The prediction result showed that the spike receptor-binding domain was the sequence of amino acids 331-583. Based on our own technical knowledge, the C-terminal sequence of the domain was extended by 10 amino acids (ILDITPCSFG, SEQ ID NO: 3) to obtain the sequence set forth in SEQ ID NO: 1. This was to enrich the cysteine from the original sequence in the C-terminal to facilitate antigen aggregation.

The obtained sequence was spliced after the IgE signal peptide; human codon optimization was performed by GenSmart Optimization (Version Beta 1.0). The primers were designed by DNAWorks (v3.2.4); the synthesized sequence was amplified by PrimeSTAR® HS DNA Polymerase (Takarabio). Endonucleases FastDigest™ EcoRI and FastDigest™ HindIII (THERMO FISHER SCIENTIFIC™) were used to digest the adeno-associated virus backbone vector pAAV-CAG-MCS-WPRE-SV40polyA. ClonExpress MultiS One Step Cloning Kit recombination kit (VAZYME, Nanjing) was used for homologous recombination ligation reactions. Products of the ligation reaction were transformed into *Escherichia coli* DH5α and spread on an ampicillin-resistant petri dish. 16 hours later, bacterial colonies were selected for further examination. The positive clones were sent to a sequencing company (GENEWIZ, Suzhou) for sequencing (SEQ ID NO: 4). The plasmid with the correct sequencing result was named pAAV-NS001 vector, and its components are shown in FIG. 1.

Example 2 Construction of AAV Expression Vector Plasmid pAAV-NS002

Figure 2:
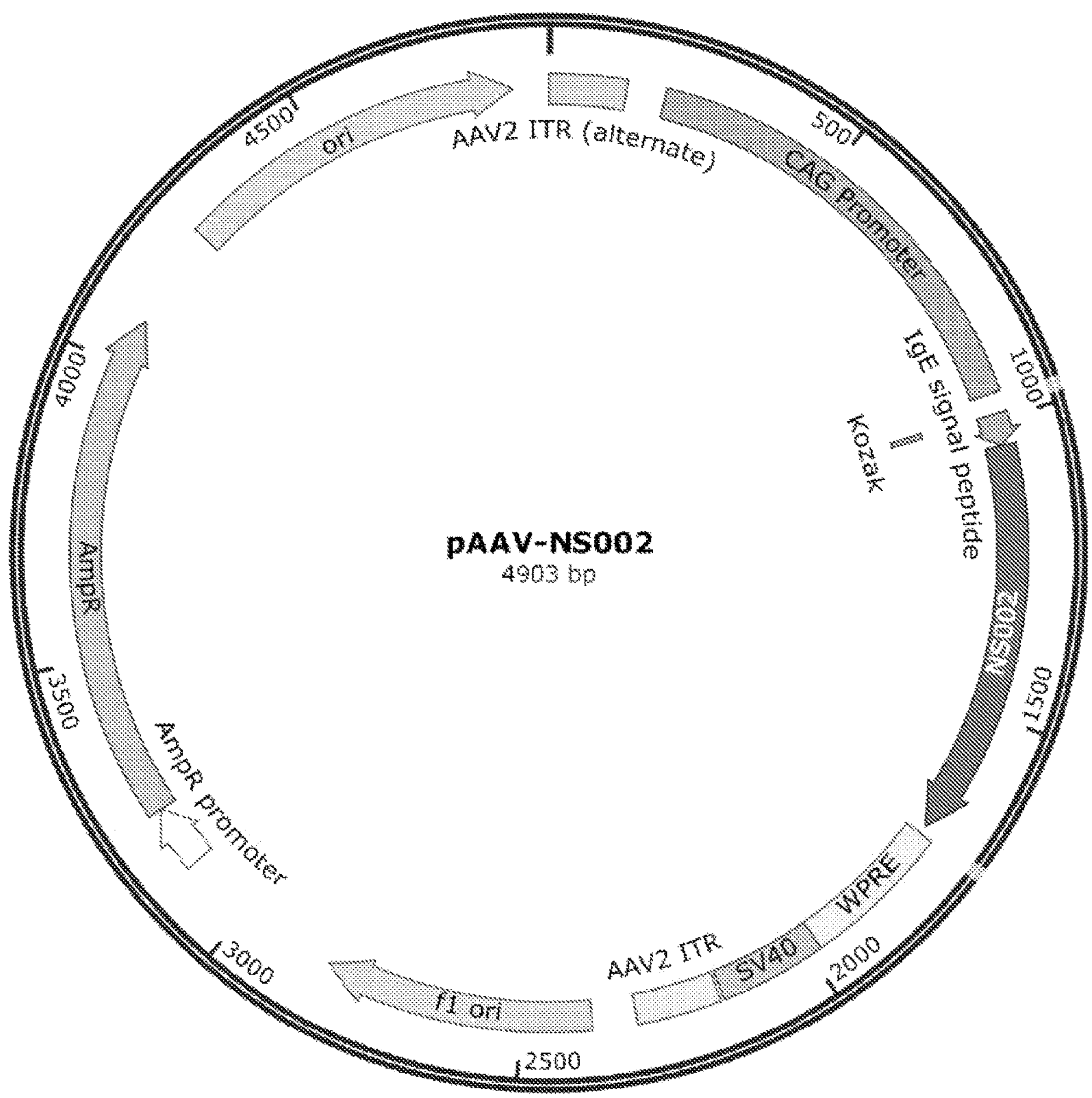
FIG. 2 is a schematic diagram of the completed vector map of pAAV-NS002; NS002 in the schematic diagram refers to the sequence set forth in SEQ ID NO: 2; other key elements are the same as FIG. 1.

The gene sequence of SARS-COV-2 (SEQ ID NO: 6, GenBank accession no. NC_045512.2) was acquired through the NCBI database. Conserved domains within the sequence were predicted by Uniprot blast through uniprotkb_refprotswissprot database. The prediction result showed that the spike receptor-binding domain was the sequence of amino acids 319-541. The sequence obtained and an IgE signal peptide were spliced into a new gene sequence; human codon optimization was performed by GenSmart Optimization (Version Beta 1.0). The primers were designed by DNAWorks (v3.2.4); the synthesized codon-optimized sequence was amplified by PrimeSTAR® HS DNA Polymerase (Takarabio). Endonucleases FastDigest™ EcoRI and FastDigest™ HindIII (THERMO FISHER SCIENTIFIC™) were used to digest the adeno-associated virus backbone vector pAAV-CAG-MCS-WPRE-SV40polyA. ClonExpress MultiS One Step Cloning Kit recombination kit (VAZYME, Nanjing) was used for homologous recombination ligation reactions. Products of the ligation reaction were transformed into *Escherichia coli* DH5α and spread on an ampicillin-resistant petri dish. 16 hours later, bacterial colonies were selected for further examination. The positive clones were sent to a sequencing company (GENEWIZ, Suzhou) for sequencing (SEQ ID NO: 5). The plasmid with the correct sequencing result was named pAAV-NS002 vector, and its components are shown in FIG. 2.

Example 3 Preparation of Recombinant Adeno-Associated Virus rAAV-NS001 and rAAV-NS002

293T cells were inoculated in a 150 mm petri dish at a density of $1\times10^7$ cells per petri dish 24 hours before transfection, and 12 μg pHelper, 8 μg pRep2Cap5, 5 μg pAAV-NS001 (or 5 μg pAAV-NS002) and 10 μg polyethyleneimine (25 kD) as a transfection reagent were added to incubate transfection. 72 hours after the transfection, the cells were harvested by centrifugation at 500×g for 5 min at 4° C. The cells were resuspended in a lysis buffer containing 50 mM Tris-HCl (pH 8.0) and 150 mM NaCl. The harvested lysate was subjected to three freeze-thaw cycles in dry ice/ethanol and 37° C. water bath successively, then 1 unit/mL of nuclease and 0.5% sodium deoxycholate were added, the resulting cell suspension was incubated at 37° C. for 1 hour. The cell suspension was centrifuged at 5,000×g for 20 minutes, rAAV supernatant crude lysate was collected at 4° C. The crude lysate was diluted with 10 mM Tris-HCl (pH 8.0) buffer to a final volume of 10 ml, then iodixanol was added into a 39 ml ultracentrifuge tube according to a mass-to-volume ratio gradient of 15%, 25%, 40%, and 60%. The mixture obtained was centrifuged at 350,000×g for 1 hour at 18° C., 3 ml of 40% lower fraction and 0.5 ml of 60% upper fraction were collected as a purified solution. The purified solution was replaced with a virus preservation solution by ultrafiltration with a 100 kDa cut-off ultrafiltration tube (MILLIPORE®). The recombinant virus preservation solution was a PBS phosphate buffer (pH 7.4) comprising 0.05% Poloxamer 188. The purified rAAVs were labeled NS001, NS002, and viral titers were determined by SYBRGreenI qPCR. NS001 and NS002 were stored in a refrigerator at −80° C. before use.

Example 4 NS001 Immunized BALB/c Mice

Five BALB/c mice aged 5-6 weeks were randomly selected for intramuscular injection of NS001 (titer of $1\times10^{12}$ GC/mL, injection volume of 200 μL). Serums of pre-immunization mice were taken as the negative control. Five BALB/c mice aged 5-6 weeks were randomly selected and immunized with recombinant green fluorescent protein adeno-associated virus vector; serums of the 5 immunized mice were used as a vector blank control.

A program of an initial immunization and a second booster immunization was adopted. Injections were carried out on day 0 and day 30. Blood was taken on day 30 and day 40; 0.1-0.2 mL of blood was taken from each mouse and was placed at 0° C. for 60 minutes. Centrifugation was performed at 4,000 rpm for 15 minutes; the upper serum was taken for ELISA analysis and antibody neutralization experiments.

Figure 3A:
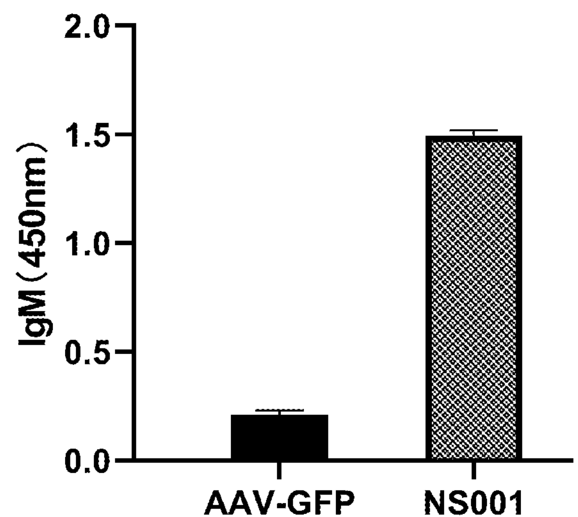
FIGS. 3A and 3B are diagrams showing the effect, as detected by ELISA, of NS001 on antibody expression in vivo after immunizing BALB/c mice with $2\times10^{11}$ viral particles of recombinant adeno-associated virus formulation NS001.
Figure 3B:
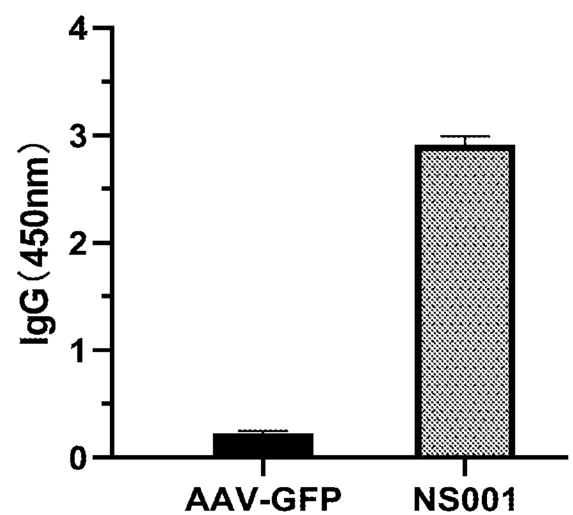

ELISA was used to detect the immune effect of mouse serum on day 30:

Recombinant spike protein RBD-His was dissolved in 0.1 M carbonate buffer (pH 9.6) to prepare a solution at a concentration of 1 μg/mL. The solution was added into a 96-well plate (100 μL per well), and incubated overnight at 4° C. The next day, the solution was incubated at 37° C. for one hour; then the plate was washed 3 times with PBST (PBS+0.1% Tween-20) (300 μL/well/time). After washing, 250 μL of 2% skimmed milk powder was added into each well, and was incubated at room temperature for 1 hour, before washed 3 times with PBST. Serum samples of 5 mice in the same group were each diluted 300 times with PBS; the diluted serum samples were added to a 96-well plate (100 μL per well), and three secondary wells were made in parallel for each dilution gradient. Incubation was carried out in a 37° C. incubator for two hours, the plate was washed 3 times. HRP (horseradish peroxidase) labeled IgG secondary antibody and IgM secondary antibody were diluted 5000 times, before being added to each well (100 μL per well) and incubated at room temperature for 1 hour; the plate was washed 3 times. 100 μL TMB solution was added to each well, followed by color development in the dark at room temperature for 20 min. 100 μL of 0.5M $H_2SO_4$ solution was added to each well. Absorbance was detected immediately with a microplate reader, the detection wavelength was 450 nm, and the background wavelength was 570 nm. The expression results of IgG and IgM in serum diluted 300 times are shown in the histograms in FIG. 3A and FIG. 3B, in which the vertical axis is the antibody absorbance (OD) value, the horizontal axis is different serum groups.

For the NS001 group administrated with the NS001 vaccine of the present disclosure, the IgM antibodies in the 300×diluted serum had an average $OD_{IgM}$ of 1.494±0.024, while in the AAV-GFP control group, the average $ODI_gM$ was 0.211±0.020). This proved that high titers of IgM antibodies were produced in the mice; the mice were IgM positive. Generally, during viral infection, before generating an adaptive high-affinity IgG response, IgM antibodies provide the first line of defense and play an important role in short-term immunity.

For the NS001 group administrated with the NS001 vaccine of the present disclosure, the IgG antibodies in the 300×diluted serum had an average $OD_{IgG}$ of 2.910±0.083, while in the AAV-GFP control group, the average $OD_{IgG}$ was 0.230±0.018). This proved that high titers of IgG antibodies were produced in the mice; the mice were IgG positive. This showed that the vaccine induced a strong immune response in the mice, and played an important role in long-term immunity and immune memory.

Example 5 Serum Neutralization Test of NS001 Immunized BALB/c Mice

The grouping of experimental animals, the immunization protocol and the method of obtaining serums were the same as those of Example 4.

Pre-immune serums and AAV-GFP infected serums were used as controls, and NS001 serogroup was the test group. Vero E6 cells were inoculated into a 96-well plate ($2\times10^4$ cells/well) and cultured overnight with 5% $CO_2$ at 37° C. On the second day, the serum samples were inactivated by heating at 56° C. for 30 min. Then, they were 4-fold serial diluted with a DMEM medium containing 2% FBS to produce a set of serially diluted serums to be tested. 100 TCID50 of SARS-COV-2 (strain number: 2020XN4276, provided and tested by a biosafety level 3 laboratory in Guangdong Provincial Center for Disease Control and Prevention) was respectively mixed with a set of 4-fold serial diluted serums to be tested, and the mixture was incubated at 37° C. for 1 h, followed by adding cultured Vero E6 cells. In each assay, wells containing cells infected by 100 TCID50 of SARS-COV-2 were positive quality control wells, while wells containing cells added with 0.1 TCID50 of the virus were negative control wells. CPE (cytopathic effect) was recorded on the 3rd day after infection. On the third day, cytopathy was found in the positive quality control wells, while no cytopathy was found in the negative quality control wells. The applicability conditions of this experiment were established. The wells exhibit CPE in each experimental group were observed and calculated, the neutralization titers of serums used in each group of 50% CPE of complete inhibition wells were calculated by the Reed-Muench method.

Figure 4:
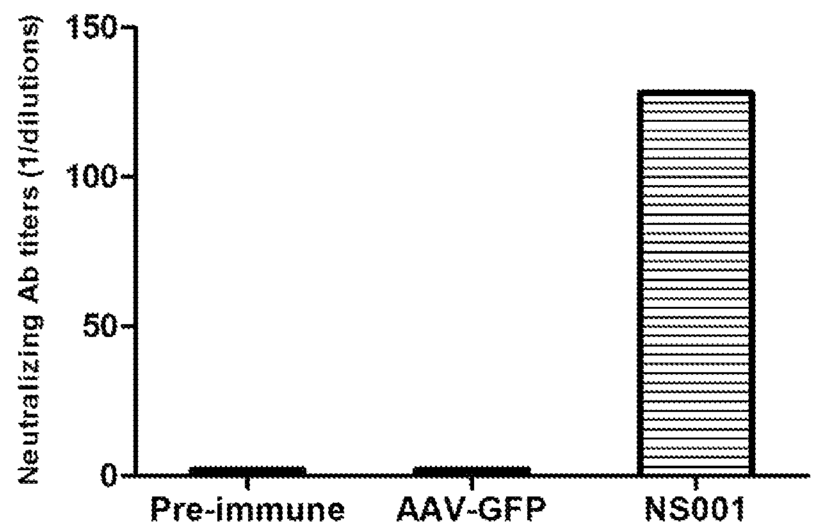
FIG. 4 is a diagram showing the result of a serum virus neutralization test 30 days after immunizing BALB/c mice with $2\times10^{11}$ viral particles of recombinant adeno-associated virus formulation NS001.

As shown in FIG. 4, the neutralization test showed that the ND50 titer of neutralizing antibodies was 1/128, indicating that NS001 formulation can produce neutralizing antibody activity against SARS-COV-2 and protect cells from SARS-COV-2 infection. The results showed that the NS001 vaccine induced humoral immune response, had a strong neutralizing activity in humoral immune response and protected cells from SARS-COV-2 infection.

Example 6 Immunized BALB/c Mice and Immunodetection

The grouping of experimental animals, the immunization protocol, the method of obtaining serums and the immune effect detection method were the same as those of Example 4.

Serums of five immunized BALB/c mice aged 5-6 weeks were collected to determine the immune effect. Please refer to the detection method of Example 4, ELISA was used to determine the immune effect of mice serums on day 30.

Figure 5A:
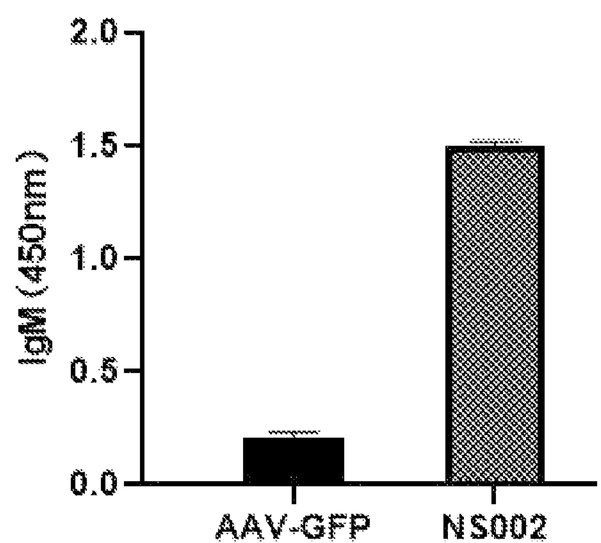
FIGS. 5A and 5B are diagrams showing the effect, as detected by ELISA, of NS002 on the antibody expression in vivo, after immunizing BALB/c mice with $2\times10^{11}$ viral particles of recombinant adeno-associated virus formulation NS002.
Figure 5B:
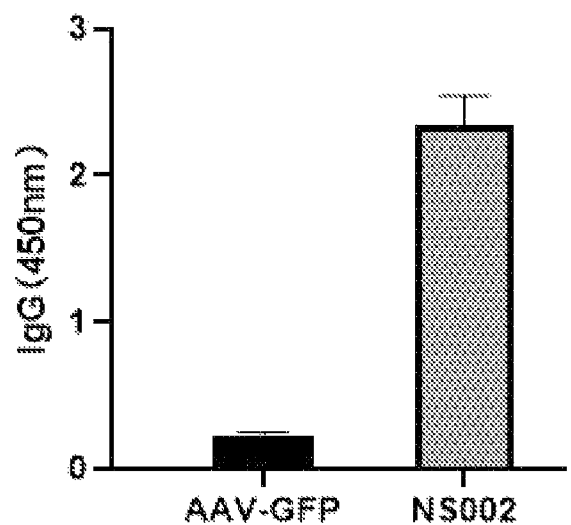

OD value of IgG and IgM expression results are shown in the histograms in FIG. 5A and FIG. 5B. For the NS002 group administrated with the NS002 vaccine of the present disclosure, the IgG antibodies in the 300×diluted serum had an average $OD_{IgG}$ of 2.340±0.205, the IgM antibodies in the 300×diluted serum had an average $OD_{IgM}$ of 1.794±0.045, while in the AAV-GFP control group, the average $OD_{IgG}$ was 0.230±0.018, and the average $OD_{IgM}$ was 0.211±0.020. The mice were IgG and IgM positive. This showed that the vaccine induced a strong immune response in the mice.

Example 7 Serum Neutralization Test of NS002 Immunized BALB/c Mice

The grouping of experimental animals, the immunization protocol and the method of obtaining serums were the same as those of Example 4.

Figure 6:
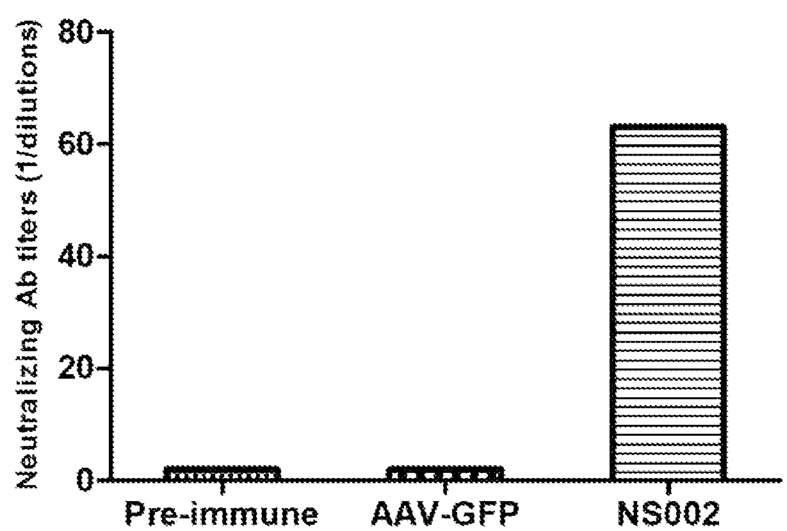
FIG. 6 is a diagram showing the result of a serum virus neutralization test 30 days after immunizing BALB/c mice with $2\times10^{11}$ viral particles of recombinant adeno-associated virus formulation NS001.

The serum neutralization test was performed according to the method of Example 5, and the results are shown in FIG. 6. The neutralization test showed that the ND50 titer of neutralizing antibodies was 1/64. The results showed that the NS002 vaccine induced humoral immune response, had a strong neutralizing activity in humoral immune response and protected cells from SARS-COV-2 infection.

The examples described above are only the preferred examples of the present disclosure. Embodiments of the present disclosure are not limited to the examples above. Any changes, modifications, substitutions, combinations or simplifications carried out within the spirit or principle of the present disclosure should be regarded as an equivalent replacement, and should be regarded as within the scope of protection of the present disclosure.

What is claimed is:

1. An expression vector expressing an SARS-COV-2 antigen polypeptide set forth in SEQ ID NO: 1, comprising an adeno-associated virus inverted terminal repeat sequence, a nucleotide sequence encoding a signal peptide, and a nucleotide sequence encoding the SARS-COV-2 antigen polypeptide.

2. The expression vector according to claim 1, wherein the nucleotide sequence encoding the signal peptide is optimized with human codons.

3. The expression vector according to claim 1, wherein the inverted terminal repeat sequence is from adeno-associated virus (AAV) serotype 2.

4. A recombinant adeno-associated virus expressing the SARS-COV-2 antigen polypeptide set forth in SEQ ID NO: 1.

5. A method for preparing the recombinant adeno-associated virus of claim 4, wherein the method comprises co-incubating pHelper, pRep2Cap5, and the expression vector expressing the SARS-COV-2 antigen polypeptide, transfecting a cell in the presence of polyethyleneimine as a transfection reagent; culturing the cell, then collecting the cell by centrifugation, performing lysis and purification to obtain a purified liquid comprising the recombinant adeno-associated virus.

6. A COVID-19 vaccine, wherein the vaccine comprises the recombinant adeno-associated virus of claim 4.

7. The COVID-19 vaccine according to claim 6, wherein the vaccine comprises a pharmaceutically acceptable diluent and/or a pharmaceutically acceptable excipient.

8. A method for eliciting a protective immune response in a subject, comprising administering to the subject a prophylactically or therapeutically effective dose of the vaccine of claim 6.

* * * * *